United States Patent [19]

Novak et al.

[11] Patent Number: 4,877,638

[45] Date of Patent: Oct. 31, 1989

[54] METHODS FOR GRIT BLASTING WITH A U.V. DETECTABLE MATERIAL

[75] Inventors: Howard L. Novak, Satellite Beach; Lee M. Zook, Titusville, both of Fla.

[73] Assignee: USBI Company, Huntsville, Ala.

[21] Appl. No.: 206,468

[22] Filed: Jun. 13, 1988

[51] Int. Cl.⁴ ............................................. B05D 1/12
[52] U.S. Cl. .................................... 427/8; 51/165.72; 51/320; 73/104; 427/157; 427/299
[58] Field of Search ................... 73/104; 51/319, 320, 51/165.72; 427/8, 299, 157

[56] References Cited

U.S. PATENT DOCUMENTS

| | | | |
|---|---|---|---|
| 2,635,329 | 4/1953 | DeForest et al. | 73/104 X |
| 2,678,420 | 5/1954 | DeForest et al. | 73/104 X |
| 3,440,082 | 4/1969 | Kube | 51/319 X |
| 3,696,565 | 10/1972 | Claeys | 51/320 |
| 3,737,349 | 6/1973 | Levenson | 149/2 |
| 4,444,701 | 4/1984 | Meguiar | 264/40.1 |
| 4,532,738 | 8/1985 | Sippel | 51/319 |
| 4,536,322 | 8/1985 | Amstutz et al. | 252/301.16 |
| 4,545,155 | 10/1985 | Nakata | 51/320 X |
| 4,772,437 | 9/1988 | Reavely et al. | 264/22 |

Primary Examiner—Shrive Beck

[57] ABSTRACT

A method of detecting cracks on the surface of an article after removal of a coating. A U.V. detectable compound is incorporated in a thermoset or thermoplastic grit blast media. A coated article is grit blasted to remove the coating. The surface of the article is exposed to U.V. radiation to detect grit blast media trapped in surface cracks. This facilitates the detection of surface cracks. U.V. detectable grit blast media is also used to provide improved coating adhesion. A U.V. detectable compound is incorporated into an abrasive mixture. A flow of the abrasive mixture is directed at the article to remove material from the surface of the article. The surface of the article is exposed to U.V. radiation in order to detect residual abrasive mixture on the surface of the article. Substantially all the abrasive mixture detected by exposure to U.V. radiation is removed from the surface of the article and at least a portion of the surface of the article is coated.

3 Claims, 1 Drawing Sheet

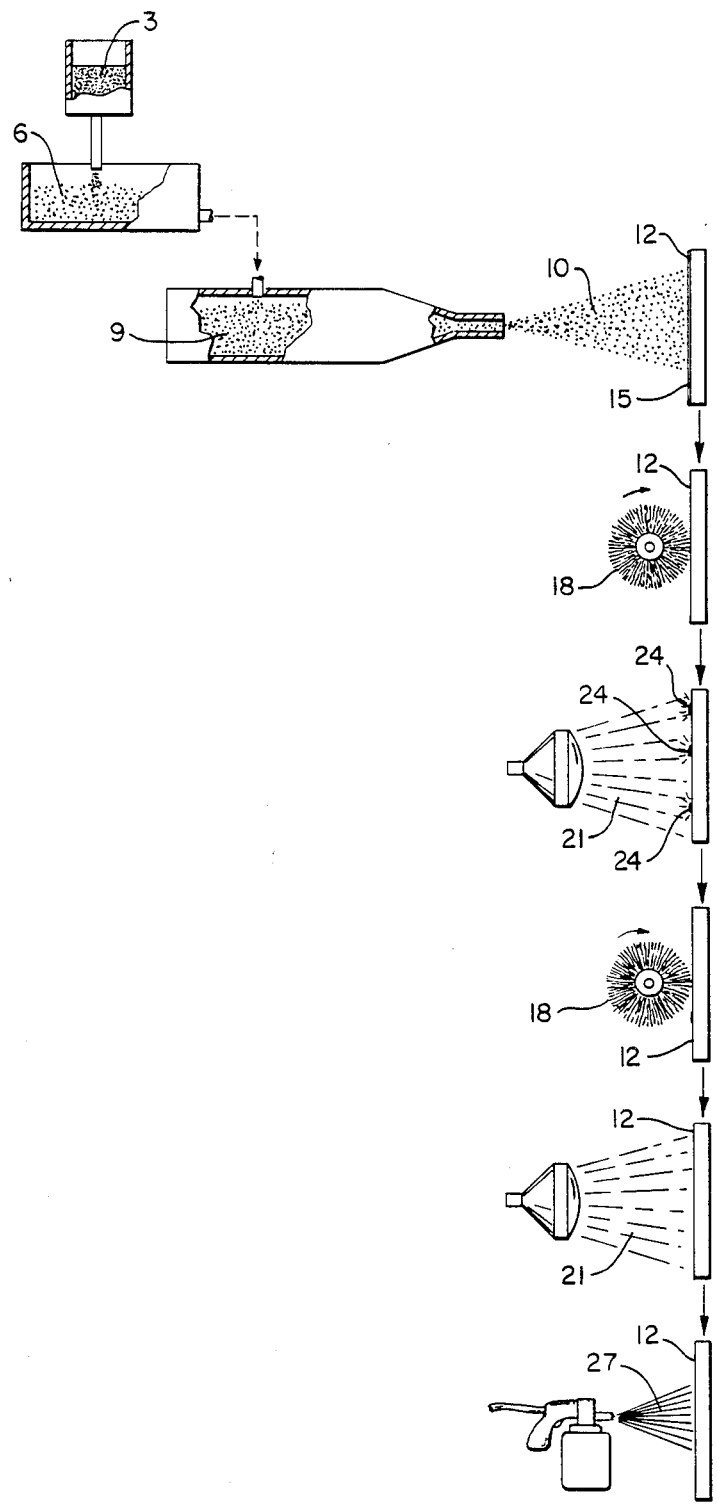

METHODS FOR GRIT BLASTING WITH A U.V. DETECTABLE MATERIAL

TECHNICAL FIELD

The field of art to which this invention pertains is the grit blasting of article surfaces.

BACKGROUND ART

A variety of grit blast media are used in the aerospace industry as abrasives to prepare surfaces for coating. Conventional grit blast media comprise thermoset and thermoplastic cured polymer resins with and without anti-static coatings. However, a variety of abrasives may be used depending on the application including walnut shells, sand, etc. Typically, the grit blast media is directed in a flow at the particular article at pressures of about 25 psi to about 60 psi and volumes of about 120 lbs. per hour to about 650 lbs. per hour, however other pressures and volumes may be used. Generally, the grit blast media is effective in removing surface coatings such as epoxy primers, epoxy topcoats, polyurethanes and sealants. However, because of the force used to propel the grit blast media, the media itself may become embedded in the surface that is being prepared for coating. A visual inspection even with high magnification may not detect any residual grit blast media on the article surface. This can occur when a grit blast media is used that tends to physically or chemically break down upon impact. This residual chemical contamination is generally not detectable even with magnification. The residual grit blast media that remains on the surface can reduce the adhesion of any subsequent coatings.

Thus, there has been a constant need in this field of art for methods of preparing the surface to be coated that result in improved coating adhesion.

DISCLOSURE OF INVENTION

One aspect of this invention is directed to a method of detecting cracks on the surface of an article after removal of a coating. A U.V. detectable compound is incorporated in a thermoset or thermoplastic grit blast media. A coated article is grit blasted to remove the coating. The surface of the article is exposed to U.V. radiation to detect grit blast media trapped in surface cracks. This facilitates the detection of surface cracks.

Another aspect of this invention relates to a method of coating an article that provides improved adhesion. A U.V. detectable compound is incorporated into an abrasive mixture. A flow of the abrasive mixture is directed at the article to remove material from the surface of the article. The surface of the article is exposed to U.V. radiation in order to detect residual abrasive mixture on the surface of the article. Substantially all the abrasive mixture detected by exposure to U.V. radiation is removed from the surface of the article and at least a portion of the surface of the article is coated.

The foregoing and other features and advantages of the present invention will become more apparent from the following description and accompanying drawings.

BRIEF DESCRIPTION OF DRAWINGS

The FIGURE represents a schematic of the coating method of this invention.

BEST MODE FOR CARRYING OUT THE INVENTION

A clearer understanding of the invention may be had by reference to the FIGURE. A U.V. detectable compound 3 is incorporated into the grit blast material 6. The resultant mixture 9 is directed (e.g., sprayed) 10 at the surface 12 in order to remove coating 15.

Subsequent to grit blasting the article surface 12 is cleaned with conventional methods such as mechanical brushing 18, air guns, vacuuming, or vapor blast. The surface 12 is exposed to ultraviolet light 21 (e.g., about 320 nm to about 400 nm) and any residual grit blast media 24 remaining on the surface is easily detected by visual examination. Robotic vision systems capable of automatically detecting contamination and/or ultraviolet traces of residual blast media could be used with this system. The residual grit blast media 24 is removed as above until U.V. light exposure reveals that there is substantially no residual grit blast media remaining on the surface. By substantially is meant about 98% of the structure. Then a coating 27 may be applied to the surface 12.

Plastic grit blast media, in general, is composed of inert thermoplastic and thermoset cured polymer resins. Urea-formaldehyde, melamine, polyesters and combinations of similar polymers are typical materials used for plastic grit media. Individual particles have sharp angular edges to allow for controlled coating removal. Typically, blast media is produced in hardnesses ranging from about 3.0 to about 4.0 MOHS. MOHS hardness 1 to 10; TALC=1 and DIAMOND=10.) Typically, particle sizes are produced in mesh grading of 12 through 60. Exemplary materials are POLYPLUS TM (MOHS 3.5), POLYEXTRA TM (MOHS 3.0) and TYPE III TM (MOHS 4.0) blast media (U.S. Technology Corp., Putnam, Conn. Other plastic blast media is available from Aerolyte Systems Div. Clemco Industries, Corp. Burlingame, Calif.

The ultraviolet fluorescent compound can be formulated as part of the virgin cured polymer resin. Only a small percentage doping of the polymer is required to produce the required traceability. Media is chopped from this virgin batch of material into the required mesh sizes. A surface coating of fluorescent material will not provide for reusability and traceability of the media because depending on how thick the coating is the fluorescent material will be worn off the particle during use. Without the fluorescent coating the abrasive particles cannot be detected on the article surface.

The problem of deposition of residual plastic blast media on various substrates relates to the original surface finish and properties of the substrate. As the angular-shaped media breaks down and becomes spherical, frictional forces increase and cutting forces diminish where transfer to the substrate can occur through frictional/mechanical/thermal deposition. A periodic inspection of the article surface with a U.V. light source can detect changes in media action and trigger replacement of media.

As the blast media is used the irregular-shaped media surface becomes more spherical and less angular. This transformation degrades the normal cutting action of the media. Then degraded rounded plastic media tends to deflect off the surface without cutting it. Thus a periodic U.V. inspection of the article surface will indicate if there is residual media on the surface of the article and that may indicate that the grit blast media needs replacement since the grit blast media has been degraded. Further testing can be done to develop a relationship for the appropriate grit blast media life based on inspection of used media and amount of residual deposit on an article. Then inspection of an article surface doing blasting can be used to detect changes in media action and trigger replacement of media.

Generally, any ultraviolet detectable (U.V.) compound can be used with the practice of this invention. By detectable is meant that it is of a type and present in sufficient quantities that under exposure to ultraviolet light, the compound is detectable (e.g., unaided eye, commercial detection device). It is preferred that under exposure to ultraviolet light of about 320 nanometers (nm) to about 550 nm the compound radiates as then it is readily visible to the unaided eye. There are a variety of conventional compounds (e.g., organic or mineral) which have this property. Organic compounds are preferred for low temperature applications (e.g., typically less than about 316° C.) as they are stable at these temperatures, are readily uniformly dispersed in the grit blast media and are visible to the unaided eye. One series of fluorescent compounds stable to at least 316° C. is manufactured by Shannon Luminescent Materials Co. (Santa Ana, Calif.). A typical tracer is a C-206 stilbene compound. A conventional weight concentration is about 0.01% to 0.1%. This can be added to the grit blast media during manufacture. An alternate method of addition would be to add the tracer to the cured grit blast in a solvent solution. The solvent could be stripped by a vacuum/heat process. Other compounds include aromatics such as Fluorel 084 anthraquinone, fluorel 086 napthxanthene, and Fluorel 088 xanthane available from BASF's Wyandotte Division (Wyandotte, Mich.). These are believed stable up to about 204° C. Typically, about 0.01% to about 0.001% by weight of the above aromatics may be used in a mixture with the grit blast media described below, however, amounts outside of this range may be used if desired so long as they are still detectable and do not adversely affect the grit blast media. Other U.V. detectable materials are available from U.S. Technology Corp. (Putnam, Conn.). Mixtures of the above compounds and derivatives of them are believed to function as well.

Mineral fluorescent compounds are preferred for higher temperature grit blasting applications since they are more stable at elevated temperatures. Higher temperatures can occur during decontamination type of grit blasting. In addition, the temperature of the grit blast can increase substantially upon impact as the kinetic energy is transformed into heat. The mineral compounds must be ground into pigment form for uniform dispersion (in contrast to many organic compounds which can be dissolved). Finally, fluorescent minerals typically require high power U.V. sources and commercial detection systems.

A variety of conventional coatings may be applied to the grit blasted surface such as epoxies, urethanes, lacquers, acrylics and sealants. Basically, any compatible coating material may be applied to applicable substrates blasted or treated by appropriate plastic media varieties.

There are many applications for this invention including those cited above. In addition, fluorescent media may be used to detect trapped material in crevices, especially when refurbishing internal structures. Jet engines, engine parts, pressure vessels must be thoroughly cleaned and checked prior to assembly. U.V. detection makes the operation of cleaning more reliable in terms of residual material removal. Thus, it has been found that blast media may be deposited in cracks and crevices which can result in stress corrosion cracking and/or fatigue failure after subsequent painting or repainting over undetected defects. Thus, residual media can mask these cracks which can lead to stress corrosion defects.

Potential applications also exist in the nuclear power field where residual materials could contribute to radiation hot-spots. In the nuclear power field, removal and cleanup of blast media is tantamount to safe operation.

Verification of spray pattern, using worn nozzles that give high pressure zones, can also be determined with U.V. light. A bad nozzle can cause nonuniform pressure distribution which will affect coating removal efficiency and damage to the substrate.

It should be understood that the invention is not limited to the particular embodiment shown and described herein, but that various changes and modifications may be made without departing from the spirit or scope of this concept as defined by the following claims.

We claim:

1. A method of detecting cracks on the surface of an article after removal of a coating comprising:
    (a) incorporating a U.V. detectable compound in a thermoset or thermoplastic grit blast media;
    (b) grit blasting the coated article to remove the coating; and
    (c) exposing the surface of the article to U.V. radiation to detect grit blast media trapped in surface cracks thereby detecting the surface cracks.

2. A method of coating an article comprising removing material from a surface of the article by directing a flow of an abrasive mixture at the article and coating the article wherein the improvement comprises:
    (a) incorporating a U.V. detectable compound in the abrasive mixture;
    (b) exposing the surface of the article to U.V. radiation in order to detect residual abrasive mixture on the surface of the article;
    (c) removing substantially all the abrasive mixture detected by exposure to U.V. radiation from the surface of the article; and
    (d) coating at least a portion of the surface of the article;
wherein the coating has improved adhesion properties.

3. The method as recited in claim 2 wherein the abrasive is a thermoset or thermoplastic resin.

* * * * *

UNITED STATES PATENT AND TRADEMARK OFFICE
CERTIFICATE OF CORRECTION

PATENT NO. : 4,877,638

DATED : October 31, 1989

INVENTOR(S) : Howard L. Novak and Lee M. Zook

It is certified that error appears in the above-identified patent and that said Letters Patent is hereby corrected as shown below:

Column 1, before "TECHNICAL FIELD" please insert the following paragraph:

--This invention was made with Government support under a contract awarded by the National Aeronautics and Space Administration. The Government has certain rights in this invention.--

Signed and Sealed this

Second Day of October, 1990

*Attest:*

HARRY F. MANBECK, JR.

*Attesting Officer*  *Commissioner of Patents and Trademarks*